(12) United States Patent
Erb

(10) Patent No.: US 8,914,242 B2
(45) Date of Patent: Dec. 16, 2014

(54) SIGNAL PROCESSING IN GUIDED WAVE CUTOFF SPECTROSCOPY

(75) Inventor: Tom Lee Erb, Austin, TX (US)

(73) Assignee: Thermo Ramsey, Inc., Coon Rapids, MN (US)

( * ) Notice: Subject to any disclaimer, the term of this patent is extended or adjusted under 35 U.S.C. 154(b) by 672 days.

(21) Appl. No.: 13/136,079

(22) Filed: Jul. 21, 2011

(65) Prior Publication Data

US 2013/0024150 A1 Jan. 24, 2013

(51) Int. Cl.
| | | |
|---|---|---|
| G01N 23/02 | (2006.01) |
| G01J 3/00 | (2006.01) |
| G06F 19/00 | (2011.01) |
| G06F 17/40 | (2006.01) |
| G01R 23/16 | (2006.01) |
| G01N 22/04 | (2006.01) |
| G01R 27/26 | (2006.01) |

(52) U.S. Cl.
CPC . *G01R 23/16* (2013.01); *G01J 3/00* (2013.01); *G01N 23/02* (2013.01); *G06F 19/00* (2013.01); *G01N 22/04* (2013.01); *G06F 17/40* (2013.01); *G01R 27/2623* (2013.01); *G06F 2219/00* (2013.01)
USPC ............... 702/30; 73/866; 250/306; 378/162; 702/1; 702/127; 702/187; 702/189; 708/200

(58) Field of Classification Search
CPC ........... G01D 7/00; G01D 9/00; G01D 21/00; G01J 3/00; G01J 3/28; G01J 2003/00; G01J 2003/28; G01N 22/00; G01N 22/04; G01N 23/00; G01N 23/02; G01N 23/06; G01N 23/22; G01N 23/223; G01N 2223/00; G01N 2223/03; G01N 2223/04; G01R 23/00; G01R 23/16; G01R 27/00; G01R 27/02; G01R 27/26; G01R 27/2617; G01T 1/00; G01T 1/16; G01T 1/28; G01T 1/36; G01T 7/00; G06F 11/00; G06F 11/30; G06F 11/32; G06F 11/34; G06F 17/00; G06F 17/40; G06F 19/00; G06F 15/00; G06F 15/16; G06F 17/10
USPC ................. 73/19.01, 23.2, 432.1, 865.8, 866, 73/866.3; 250/306, 492.1; 356/72, 73, 356/300, 326, 337; 378/1, 51, 53, 70, 82, 378/83, 86, 88, 162; 702/1, 22, 27, 28, 30, 702/31, 32, 57, 66, 75, 76, 127, 187, 189; 708/100, 105, 200

See application file for complete search history.

(56) References Cited

U.S. PATENT DOCUMENTS 2,820,173 A * 1/1958 Raabe ............................... 315/9
3,114,832 A * 12/1963 Alvarez .......................... 378/53

(Continued)

*Primary Examiner* — Edward Cosimano
(74) *Attorney, Agent, or Firm* — David George Johnson

(57) ABSTRACT

The present invention includes a guided microwave spectroscopy system (1) that eliminates the need for an automatic gain control feature by providing multiple signal processing paths having differing fixed voltage gains. An emitted signal which exits a test chamber (2) containing a material under test is simultaneously amplified by at least a first fixed gain amplifier (4) and a second fixed gain amplifier (7). The output signal of each amplifier is separately digitized and then normalized for further digital signal processing by a computer (13) in order to determine parameters of the material under test which may have variable microwave radiation characteristics that are a function of the frequency of the signal emitted into the test chamber. During the signal processing step a system clock (121) causes the computer to sample only an integral number of complete output signal cycles. A calibration protocol (136-154) is conducted based on laboratory samples of each potential material to be processed by the system (1).

20 Claims, 11 Drawing Sheets

(56) References Cited

U.S. PATENT DOCUMENTS

| | | | |
|---|---|---|---|
| 3,486,822 A * | 12/1969 | Harris | 356/308 |
| 3,710,104 A * | 1/1973 | Pavlik | 378/46 |
| 5,125,009 A | 6/1992 | DeVilbiss | |
| 5,331,284 A | 7/1994 | Jean et al. | |
| 5,455,516 A | 10/1995 | Jean et al. | |
| 5,758,023 A | 5/1998 | Bordeaux | |
| 5,805,871 A | 9/1998 | Baxter | |
| 6,308,048 B1 | 10/2001 | Gore et al. | |
| 2002/0095304 A1 * | 7/2002 | Khazei | 705/1 |

* cited by examiner

SIGNAL PROCESSING IN GUIDED WAVE CUTOFF SPECTROSCOPY

FIELD OF THE INVENTION

This invention relates generally to the field of Guided Microwave Spectroscopy, and more particularly to the observation and analysis of multiple signal sources when analyzing the dielectric properties of a material under test.

DESCRIPTION OF RELATED TECHNOLOGY

The use of a microwave waveguide cutoff frequency to characterize properties of materials is commonly referred to as Guided Microwave Spectroscopy (GMS) and is described, for example, in U.S. Pat. Nos. 5,331,284 and 5,455,516. GMS systems measure the dielectric properties of the material being tested, referred to as the MUT (Material under Test). The measurement technique places, often as a flowing slurry, the MUT in a measurement cell. This cell includes an electromagnetic waveguide which is frequently called a microwave waveguides However, the microwave region is broadly considered to relate to frequencies above 1 Gigahertz (GHz). Typical GMS systems can operate from well below to well above 1 GHz.

GMS systems operate by quantifying the electrical waveguide characteristics of the cell as a function of frequency while the MUT is in the cell. This general type of measurement technology is referred to as guided wave spectroscopy (GWS). One aspect of the GWS technique is that the waveguide cutoff characteristics of the cell are being exploited along with other characteristics. Of these, one of the most important is the cutoff frequency. This is a much higher quality method of determining the MUT dielectric constant than alternative methods.

An electromagnetic waveguide is any bounded structure through or along which electromagnetic waves can travel. Such devices can be implemented with different geometrical shapes. Many such geometries exhibit a characteristic known as "cutoff". In general, cutoff refers to a frequency (the cutoff frequency) below which the waveguide will not pass energy.

A typical measurement response is that as the frequency of electromagnetic energy emitted into the cell is reduced to near cutoff, the propagation velocity of the emitted energy slows. At the cutoff frequency the velocity drops to zero and no energy is passed in an ideal system. However, in practical implementations, as the velocity slows in response to the frequency being moved toward cutoff, any propagation losses are increased so that the loss associated with cutoff becomes significant before the frequency actually drops to the cutoff point. The often gradual increase in propagation loss as cutoff is approached creates a difficulty in measuring the actual cutoff point. The signal level in the frequency region near cutoff can be so low that it may be difficult to accurately determine the cutoff point.

There are various techniques for extracting spectral metrics that track with cutoff and are more practical to quantify. In any case, cutoff determination involves analyzing the spectral pattern of the first (lowest frequency) observable signals exiting the measurement cell after passing through the MUT. Since the actual amplitude of these signals can vary greatly with MUT characteristics, it is essential that no detectable signals be allowed through the cell when the excitation frequency is below cutoff.

For example if a cell containing a particular MUT has an actual cutoff frequency of 400 MHz, then any frequencies emitted below 400 MHz should not pass. Thus, the measured response with 300 MHz excitation should be essentially zero. However, any practical implementation of a 300 MHz source will have some harmonic content at 600 MHz and 900 MHz. These harmonics will readily pass through the cell and be seen as a non-zero level. This behavior would imply that the cutoff frequency was less than 300 MHz, not the correct value of 400 MHz. Thus a need exists for a system that precludes the presence of harmonics in the signal level measurement. To eliminate variations in excitation power and input sensitivity as a function of frequency and time, the measurement of the signal through the cell at each frequency must be normalized to reference channel measurements for each frequency.

In previous GMS implementations the amplitude of raw received signal data was represented by a direct current (DC) voltage. The DC voltage was typically digitized and used to represent a single data point in an overall signal response curve. In improved GMS implementations the radio frequency (RF) signal level is represented by an alternating current (AC) signal that may have a frequency in the range of several kHz to several MHz. The required sampling rate of the received signal in combined with large variations in signal amplitude presents a challenge to the signal processing abilities of available analog to digital converters (ADC). The conventional prior art approach to dealing with the large range of received signal amplitude has been to employ an automatic gain control (AGC) function to decrease the dynamic range of the signal that reaches the ADC.

Automatic gain control can function effectively in some applications. However, such gain control data is based on historical or previous signal amplitude information. The result of using prior data to control AGC parameters in a dynamic system is that in a step or increment based system, for example, every step that is processed with an inappropriate gain value that was derived from a previous signal amplitude must then be repeated with a corrected gain setting based on the actual amplitude of the signal being received. In some cases, multiple repeated signal measurements may be required, creating a delay that can affect the data processing response times of the GMS system.

More specifically, in prior GWS systems, frequency generation was created by an Integer-N Phase Locked Loop (PLL) controlled by a Voltage Controlled Oscillator (VCO) that provided a one octave frequency range. This frequency was used directly, frequency divided, or frequency multiplied by factors of two to provide frequencies in other octaves. The excitation signal was passed through a selected one of several filters to reduce the harmonic content of the signal. The lowest order harmonic for each fundamental frequency is twice the fundamental frequency.

The frequency response of the selected harmonic suppression filter is required to diminish or roll off well below twice the lowest frequency that that filter can serve. The filter roll-off needs to start at approximately 70% of the lowest offending harmonic, meaning that a single filter cannot serve an entire octave. In practice each octave of operating frequency range requires two dedicated filters circuits. In the only practical implementation of this harmonic suppression architecture, the four included excitation octaves (200 MHz to 3200 MHz) required the use of eight excitation filter circuits. For example, a fundamental excitation frequency of 200 MHz has a second harmonic at 400 MHz. Thus, a filter that works for 200 MHz needs to begin roll-off in the general range of 280 MHz. Therefore, such a filter could only serve for frequencies from 200 MHz to 280 MHz. For frequencies above 280 MHz, a different filter circuit must be selected in order to serve the rest of the octave (280 MHz to 400 MHz).

In order to obtain the required harmonic suppression, an additional array of selectable filter circuits must be used for processing the received, post MUT signal. The need of a second set of receiver filter circuits is necessary because no matter how much harmonic attenuation an excitation filter might provide, it is inherently difficult to isolate the signal appearing at the filter output from the signal present at the filter input to a level that substantially prevents any of the harmonic signal energy from "bleeding over" to the filter output signal. For example if sixty decibel (dB) harmonic attenuation (99.999% power reduction) is needed, then −40 dB (0.01%) input signal bleed over to the filter output would greatly reduce the effectiveness of a 60 dB filter circuit. However, if a 30 dB (0.1%) excitation filter circuit is used in conjunction with a 30 dB input circuit filter, the −40 dB bleed over signal level on each filter would have little effect.

The radio frequency (RF) signal exiting the measurement cell is typically level adjusted by use of amplification and attenuation. The narrow dynamic range of the typical square-law signal detector requires that the amplification/attenuation of the RF signal be adjusted at each frequency to bring the signal level within the ideal range for the detector.

Setting the amplification/attenuation level to obtain the correct response at each frequency exacts two penalties. First, after a new frequency value has been established, an analog to digital converter (ADC) reading is obtained. Depending on the magnitude of the measurement, an adjustment in amplification/attenuation may be necessary. Subsequently, another ADC reading must be taken with the new setting. Second, since the amplification/attenuation setting can be different, a new calibration path reading is required at each frequency. The calibration routine slows the absolute measurement time as well as contributing the noise of the reference channel reading to the noise of the net received signal level reading. Thus, the signal measurement protocol for each new frequency required the following ten steps: wait for the infinite impulse response (IIR) filter to stabilize; obtain the ADC reading of cell output signal; set the amplification/attenuation level based on the ADC reading if required; wait for the IIR fitter to stabilize as necessary; select a new frequency; wait for the selected frequency to stabilize; obtain the ADC reading of the cell output signal if needed; select the signal reference channel; wait for the IIR filter to stabilize; and finally obtain the ADC reading of reference signal.

The bandwidth of the signal going into the detection circuit which converts the received RF signal to direct current (DC) is on the order of half an octave. In practical terms, this detection bandwidth will range from 100 MHz to almost 2000 MHz. Since noise increases with detection bandwidth, the noise entering the detection circuit will be quite high.

A further problem occurs when conventional digital sampling techniques are employed to measure the amplitude of the received signal. The sampling period and the sampled waveform are often not in phase with each other, which can then create a set of amplitude measurement values that includes an integral number of waveforms as well as a portion of at least one and possibly two additional cycles. As seen in FIG. 6, three complete cycles 113, 114 and 115 are shown along with a partial cycle 116. While the sample period 117 includes three complete cycles, a sample period 118 of identical length includes only part of cycle 113 and includes a portion of cycle 116. The longer sample period 119 includes three complete cycles as well as the partial cycle. Regardless of whether peak, average or root mean square values are used to calculate signal amplitude, the inclusion of partial cycles within the amplitude calculation algorithm introduces error.

The conventional method used to deal with this problem is called "windowing". This involves applying factors to the waveform that reduce the amplitude of the waveform ends to zero. These factors gradually increase as they move away from the ends of the waveform. This technique serves to mitigate the sampling phase versus waveform phase issue. However, a significant portion of the information is discarded. This reduces the signal to noise ratio, deteriorating the quality of the measurement.

An example of a digitized master clock which triggers a sampling period is disclosed in U.S. Pat. No. 5,125,009, entitled METHOD AND APPARATUS FOR SYNCHRONOUSLY DISTRIBUTION (sic) DIGITAL SIGNALS IN HIGH SPEED SYSTEMS. The '009 patent deals with a distributed digital systems (DDS) rather than direct digital synthesis (also commonly abbreviated DDS), but does address the problem of using a single master clock to perform various tasks such as sampling (see column 1, lines 35-43). While the '009 patent attempts to achieve simultaneous triggering of various digital modules at a desired frequency, the fact that a triggering event may in mid cycle due to phase variations is not addressed. The main thrust of the '009 device is to utilize a relatively lower master clock frequency which may be distributed throughout a system at a relatively lower frequency in order to minimize attenuation caused by impedance mismatches.

A system that does address frequency and phase relationships is disclosed in U.S. Pat. No. 5,805,871, entitled SYSTEM AND METHOD FOR PHASE-SYNCHRONOUS FLEXIBLE-FREQUENCY CLOCKING AND MESSAGING. The '871 device uses traditional phase locked loop technology to maintain a desired frequency so that different frequency sources have a fixed frequency relationship to each other (see column 3, lines 16-24). The problem of using any of the frequency sources to define a sampling period that will include only an integral number of complete cycles is not addressed.

A further problem arises when using conventional heterodyne schemes to recover the received signal data. Typically, frequency variations in the down converted intermediate frequency will equal the sum of variations of the radio frequency excitation signal and the reference local oscillator (LO) signal. Since these signals can have a frequency of several GHz, even small relative frequency variations can produce large relative frequency variations in the final intermediate frequency signal. These frequency variations limit the absolute minimum value of the detection bandwidth, thereby degrading the signal to noise ratio by requiring larger detection bandwidths which necessarily admit additional noise components along with the desired signal. A need exists therefore to improve the accuracy of the down conversion process. An example of current oscillator technology is disclosed, for example, in U.S. Pat. No. 6,308,048, entitled "SIMPLIFIED REFERENCE FREQUENCY DISTRIBUTION IN A MOBILE PHONE". The '048 patent discloses a receiver in which the RF and LO signals are produced by individual PLLs that are synchronous with a single reference signal, but does not suggest the use or applicability of such a scheme in a real time stepped frequency guided microwave spectroscopy environment.

An additional problem occurs when employing a digitized signal processing scheme. In a digital radio or other continuous signal application, the digital waveform is normally continuously filtered. In a typical prior art IIR filter based system, the post detector final signal filter is continuously accumulating and simultaneously discarding information. Once the input signal is valid a prior art system must introduce a signal processing delay while sufficient invalid information is discarded or decays so as to not contaminate the desired signal. At the same time that the invalid information is being discarded some portion of the recently arrived valid information is also, being discarded. This results in a system that loses the signal to noise benefit of that discarded portion of the valid information. A device using such filtering is disclosed, for example, in U.S. Pat. No. 5,758,023, entitled "MULTI-LANGUAGE SPEECH RECOGNITION SYSTEM", which discloses a device in which accuracy is sacrificed in order to minimize processing time in a real time data reduction setting. Such a system is poorly suited to the examination of a waveform the represents discrete events. Inherent in a typical continuous filtering system is data that is constantly being discarded in order to accommodate the processing of new data.

The measurement bandwidth of prior systems is quite broad. Each additional octave requires four additional filter circuits composed of two excitation filters and two input filters. The detection bandwidth of prior systems is quite broad which causes the presence relatively large noise component, thereby degrading the signal to noise ratio. For any particular frequency within the broad detection bandwidth, the bandwidth is fixed while changing every half octave over the sweep range. The sweep range is limited to four octaves.

Previously known systems use phase shift measurements to infer the dielectric constant of the MUT. Typically such systems operate over a very narrow frequency range which defines the measurement bandwidth. A narrow measurement bandwidth not only affects the quality of the dielectric constant measurement, but also limits any response to changes in the MUT dielectric constant to a narrow frequency range. This limitation precludes examining MUT dielectric constant characteristics over a wide frequency range. Many prior art systems use a homodyne system to measure phase change. A homodyne system is effective within the narrow measurement bandwidth limitations of such prior art systems. However, a homodyne system is generally ineffective for measuring signal strength as a function of frequency insofar as there is essentially no amplitude information present near frequencies where the received waveform phase passes through zero amplitude.

A further problem present in prior art guided microwave analysis systems is the determination of a standard waveform or set of parameters to which the MUT may be compared in order quantify a rejection or acceptance decision. The MUT is typically a complex organic article that may have variations in ingredients during the course of an extended production period. Thus a means is needed to rapidly and accurately establish a qualification or calibration standard that may be implemented according to a straightforward protocol in a rapid and automated manner.

SUMMARY OF THE INVENTION

The present invention improves the dynamic range of prior systems by employing advanced digital signal processing. The present invention provides a design that performs all data measurement steps in a single pass, that is, in response to a single emitted signal occurring at a single sampling interval. The gathering of all necessary data in a single pass is accomplished by utilizing two or more signals paths derived from the same received signal created in response to a single emitted signal. Each received signal path has a different stage or path gain when compared to any other received signal path. Each of the resulting received signals is digitized simultaneously by separate analog to digital converters or ADC channels.

In one preferred implementation of the present invention, two separate received signal paths are utilized, wherein the first path has a first voltage gain and the second path has a second voltage gain that is one sixty fourth ($1/64$) of the first voltage gain. This voltage gain offset would allow normalization of the data by simply shifting the data value for the second path by six binary columns or placeholders. The effective ADC capability would be increased by six bits and the dynamic range of the system would be increased by thirty six decibels (dB).

In a second preferred embodiment of the present invention, the number of waveforms that are sampled during any sampling period is forced to be an integral number so that any subsequent amplitude calculation is based only on an analysis of complete 360 degree cycles. This synchronization of sampling periods with sample size is accomplished by controlling the sample rate, the sample count, the waveform frequency or a subset of those three parameters.

Another feature of the present invention is the improvement in signal to noise ratio achieved by employing RF excitation and local oscillator (LO) reference signals that are generated synchronously from a common source. In this manner, any relatively small variations originating in the timing source are largely cancelled. Two phase locked loop (PLL) circuits use a common frequency reference or references that are derived from a common source, thereby insuring little variation in the difference intermediate frequency that is derived from the difference between the RF and the LO frequency. Further, the RF and LO signals are phase synchronous, thereby attenuating phase noise. The primary or time base frequency source operates at a frequency of 86.08 MHz, and both PLLs utilize a 21.52 MHz reference frequency (86.08 MHz/4). The LO frequency can be set precisely to 10.76 MHz above or below any RF excitation frequency (10.76=8×86.08/16). The first IF signal produced by the first mixer has a fixed frequency of 10.76 MHz which is passed through a band pass or low pass filter and then into a second mixer.

Another feature of the present invention is the ability to filter and process the entire discrete waveform produced by a stepped frequency electro-magnetic characterization event as a single, untruncated batch. Since no data is discarded, the resulting signal to noise ratio is superior to that obtainable with continuous filtering and processing techniques.

The present invention uses no amplification or attenuation switching between frequencies. All frequencies in a sweep can be processed at the same excitation power and gain levels. With fixed excitation and gain, there is no need to obtain a reference channel reading for each cell reading at each point in the sweep. Thus, reference channel readings can be accumulated with little impact on the sweep time. Further, reference channel readings can be averaged by using infinite impulse response (IIR) or finite impulse response (FIR) filters over time to greatly reduce their net noise contribution to the measurement cell signal amplitude data.

The down converted intermediate frequency output of the first mixer operates at a fixed frequency. The RF harmonics are also down converted, but the present invention substantially reduces the effect of the harmonics on system performance. Since all of the RF harmonics are operating at two or more times the fundamental RF signal frequency, none of the down converted lower frequency optimized circuitry of the receiver is capable of processing any down converted RF harmonic. Thus, RF harmonic bleed over through RF filters is not an issue since such filters are not present. All RF harmonics are at frequencies too high to be processed by the low frequency receiver circuitry.

The down converted harmonics appear as intermodulation products between the RF signal harmonics and the LO signal harmonics. The second RF harmonic will mix with the second LO harmonic to produce a down converted signal that is twice the frequency of the main down converted RF signal (the first IF signal). Subsequent intermodulation products of interest will be at integer multiples of the first IF frequency.

The first IF frequency is low enough that the integral multiple harmonics are readily handled with a single low pass filter circuit. Bleed over of input to output signal through the much lower frequency IF filter is less of an issue than with the RF harmonics due to the inherently superior performance of filters operating at lower frequencies.

The harmonic attenuation the second harmonic intermodulation down conversion product is further reduced by the use of a double balanced mixer. This has the effect of reducing the effect of second LO harmonic by reducing the mixer conversion efficiency when processing the second and other even RF harmonics.

The second down conversion stage includes filters that further suppress any residual harmonics received from the first IF stage. Any possible bleed over from the higher frequency sections is well outside the response range of the circuitry handling the second IF signal. The first down conversion stage includes an IF frequency (the difference between the RF and LO frequencies) that is well within the granularity capability of the PLL circuit. The second down conversion event creates an IF frequency that is within the range of the very high resolution analog to digital converter. Precise control of the second mixer LO frequency results in a final IF frequency can be established with extreme precision. The direct digital synthesis (DDS) circuitry provides LO frequencies that allow for second IF granularity of better than a micro-hertz, which simplifies phase matching of the multiple signals present in the system.

The present invention utilizes a final IF frequency that is low enough to be digitized by a high resolution ADC. An example frequency for such an implementation is 60 kHz. The IF signal waveform is digitized directly thereby eliminating the need for an analog detector. The preferred embodiment provides a considerable signal processing dynamic range, thereby requiring digitizing of the signal over extreme ranges in order to avoid the previously discussed prior art approach of measuring, adjusting parameters based on the measurement and then measuring again.

Since all of the analog circuitry except the mixers is linear, ADC dynamic range increases at 6 dB per bit as compared to 3 dB per bit in prior art technology. In order to eliminate the need for post measurement gain changes, a multiple channel ADC can be employed. Each analog ADC input is fed with a different gain in its input path. Alternately multiple ADCs can be employed or a combination of multiple multi-input ADCs.

The gain range of each of the ADC input paths permits the working dynamic range to overlap the working dynamic range of at least one of the other ADC input paths. All of the ADC inputs are digitized substantially simultaneously. The signal processor then determines which source of input data to use based on the amplitude of the available data.

Normalizing gain differences between inputs is accomplished by causing the system to obtain, store and learn the gain ratios between signal processing paths by comparing the measured levels of signals that occur in each ADC path overlap range. The gain ratio measurement can be done either continuously during normal operation or during an initial calibration procedure. In an alternate embodiment of the present invention, the gain difference between ADC input paths is ignored and only the digitized reference path data from the ADC input is selected for use with the cell signal. This technique is especially applicable when only two ADC inputs are used. The reference or calibration channel signal is set to a level that is near the top of the ADC range for the highest gain input path. The cell signal is then normalized to the reference signal by using the same ADC input for both the reference and cell signals regardless of which ADC input is used. In this manner the gain difference between the ADC inputs is eliminated.

In operation, the digitized reference channel signals from all inputs are filtered and stored. When post MUT cell signal level reading are taken the appropriate previously stored reference channel normalization value will be available for the signal frequency being processed.

The present system digitizes the entire final IF waveform, thereby eliminating need to wait for a previous signal to decay. Digital data prior to the desired valid signal is ignored. As valid data arrives the data is accumulated without any of the data being discarded. At some point during the valid data accumulation event the system may begin to step to the next frequency and thus will immediately begin to generate an invalid analog signal. However, there is some finite delay in the actual arrival of that invalid data at the ADC output. The present system takes advantage of this delay by continuing to accumulate valid data until the arrival time of the valid data. Once acquired, the data from all ADC inputs can be processed to the detection bandwidth limit and the total energy or net power associated with the waveform can be computed. Once normalized to the reference channel data, the total energy computation becomes a received signal frequency point in the total response spectrum of the post MUT measurement cell output signal.

The present system employs coherent signal generation and conversions, allowing the acquired signal to be phase compared to a similarly acquired phase reference signal in order to determine the phase shift in the post MUT signal exiting the measurement cell. Phase shift change with frequency change is a function of velocity, while velocity is a function of dielectric constant. Although the controlling dielectric constant occurs at the single cutoff frequency, in some cases additional information about the MUT can be derived from the dielectric constant at different frequencies. Thus, the change in phase at various frequencies can provide dielectric constant related information at these frequencies. The quality of any velocity measuring system is a function of measurement bandwidth. The present guided wave system operates over large measurement bandwidths and is able to quantify the effects of changes in dielectric constant at different frequencies with improved resolution that is attributable to the increased measurement bandwidth. The coherent heterodyne architecture of the present invention can measure amplitude and phase change by examining the same received signal.

Further, the amplitude information obtained can be used to correct the phase information for each individual stepped frequency.

In the present invention the bandwidth of the final intermediate frequency signal is determined by digital signal processing utilizing finite impulse response techniques. The first stage of the digital signal processing scheme includes the decimation filter present in the analog to digital converter. Additional filtering is applied to the digitized waveform signal. The resultant detection bandwidth varies from between a few hertz to a few kilohertz as needed. The detection bandwidths of the present invention are several orders of magnitude narrower than prior art devices, resulting in a greatly improved signal to noise ratio. The present invention is capable of including a stepped frequency range of seven octaves.

The present invention also includes an automated calibration program that permits idealized parameters for a particular material under test to be rapidly determined.

Rather than relying on a standard reference or test item to be introduced into the measurement cell, a number of typical and acceptable items that are representative are examined and statistically analyzed. An idealized waveform along with a set of derived material characteristics are determined and stored for immediate as well as future reference.

DETAILED DESCRIPTION OF THE INVENTION

Figure 1:
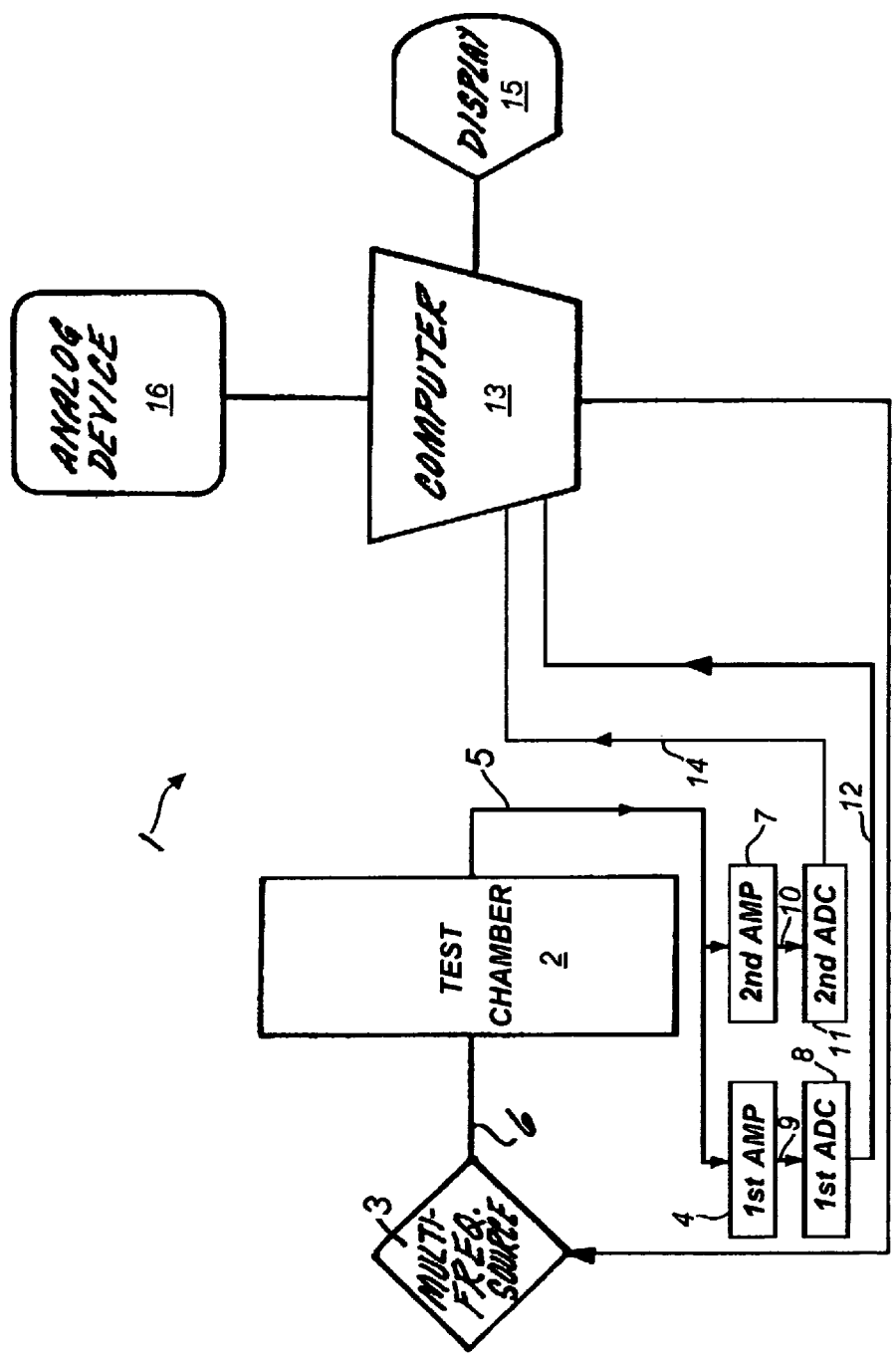
FIG. 1 is a block diagram illustrating a preferred embodiment of the present invention.

The present invention is shown generally at 1 in the block diagram of FIG. 1, where the test chamber 2 includes some means for introducing a material to be tested, the means typically being a pipe that transports the material under test through the chamber as a flowable material such as a liquid or slurry. A swept or stepped frequency source 3 is interconnected via path 6 with the chamber 2, the source 3 typically being an oscillator capable of generating multiple radio frequencies in the range of thirty megahertz (30 MHz) to four gigahertz (GHz). Depending upon the material under test and the physical characteristics of the chamber 2, some portion of the radio frequency spectrum is emitted into the chamber and passes through the material under test that is residing at that moment within the chamber. The test chamber 2 is shaped and dimensioned to create frequency dependent responses when subjected to electromagnetic radiation, typically ranging from RF and into the microwave region of the radio spectrum.

After passing through the material under test, the remnant of the emitted signal generated by frequency source 3 exits the chamber 2 via path 5, the signal typically being attenuated, and phase shifted, and otherwise altered by the interaction of the emitted signal with the material under test within the chamber. The remnant signal following path 5 is frequency down converted and then amplified by at least two amplifiers, for example a first amplifier 4 and a second amplifier 7. The first amplifier 4 typically has a relatively low voltage gain, typically at or near unity, the first amplifier 4 therefore acting primarily as a buffer for the remnant signal present on path 5. The buffered output signal on signal path 9 is interconnected to a first analog to digital converter (ADC) 8. The remnant signal of path 5 is a pure analog signal which is then converted by ADC 8 to a digital signal following signal path 12 to a microprocessor or computer 13 where the digitized signal is available for further digital signal processing (DSP) techniques.

The remnant signal on path 5 is also amplified by the second amplifier 7, which typically has a relatively higher voltage gain, for example a voltage gain of thirty two ($2^5$), which corresponds to a gain difference between first amplifier 4 and second amplifier 7 of approximately thirty decibels (30 dB). The output of the second amplifier 7 on path 10 is digitized by a second ADC 11 and forwarded to the computer 13 via signal path 14. The computer can forward the results of any DSP analysis performed on the received signals to a human machine interface (HMI) such as display 15 or to a suitable analog device 16 such as a meter, alarm or feedback mechanism.

Figure 2:
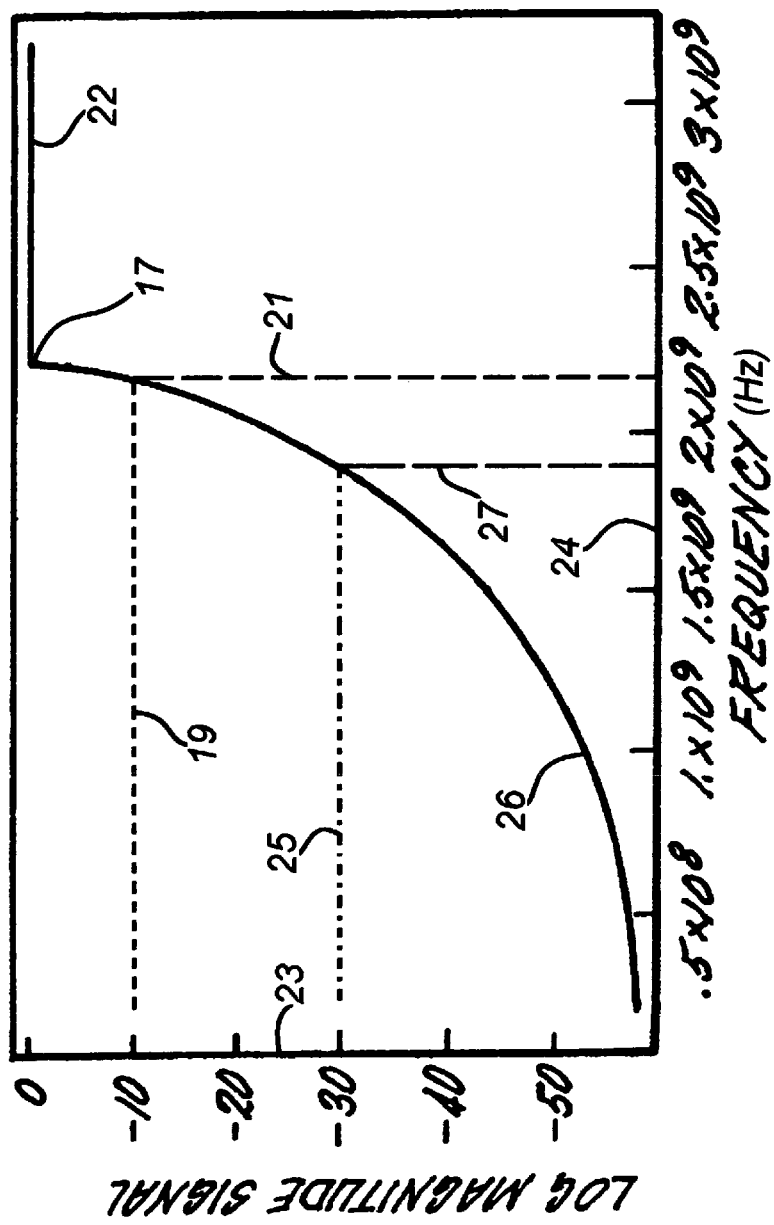
FIG. 2 is a graph depicting the idealized logarithm of the magnitude of signal amplitude versus signal frequency derived by the device depicted in FIG. 1 for an idealized material under test.

Referring also to FIG. 2, the curve 26 depicts the response of a material within the chamber 2 when electro-magnetically characterized by the swept frequency source 3. The x-axis 24 indicates a swept or stepped frequency range extending from less than five hundred megahertz to more than three gigahertz (GHz). The response curve 26 shows that the cutoff frequency occurs at point 17 in this particular case, beyond which the response 22 is flat or of a relatively constant value regardless of the excitation frequency.

The cutoff frequency 17 is dependent primarily on the geometry and dimensions of the particular test chamber 2 and on the dielectric constant of the material in or flowing through the chamber. In this case the material under test is assumed to have an idealized relatively homogeneous dielectric constant which produces a curve 26. Reference to the y-axis 23 indicates that the curve 26 has a magnitude that is frequency dependent. In particular, the magnitude of the radio frequency signal passing through the material under test and exiting the test chamber 2 via signal path 5 is highly attenuated at relatively lower frequencies while the magnitude of the signal on signal path 5 is substantially greater at relatively higher frequencies. For example, the magnitude 25 of the signal received at frequency 27 (approximately 1.8 GHz) is approximately −30 dB. The magnitude 19 of the signal received at frequency 21 (approximately 2.2 GHz) is approximately −10 dB. However, the particular shape and magnitude of the curve 26 is variable and dependent on the dielectric characteristics of the material within the test chamber 2, and in the case of a flowing material is capable of varying over a wide range of amplitudes for a given frequency.

Figure 3:
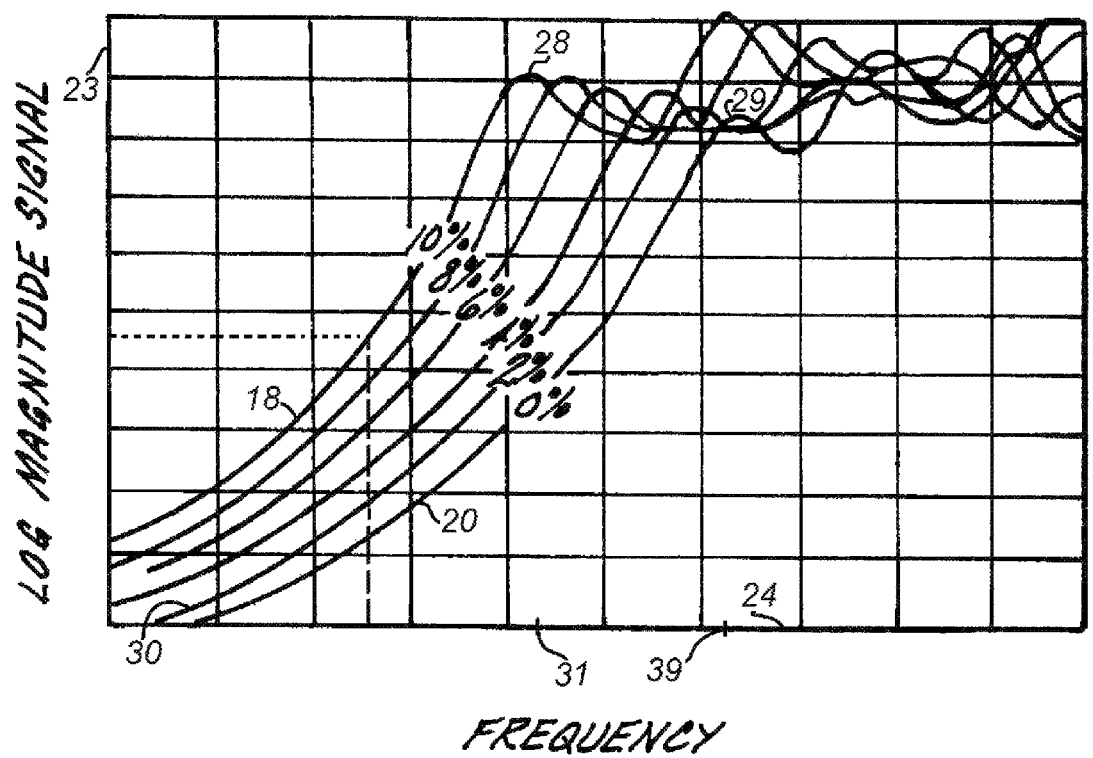
FIG. 3 is a graph illustrating the actual logarithm of the magnitude of signal amplitude versus signal frequency derived by the device depicted in FIG. 1 for an actual material under test that contains varying concentrations of water.

FIG. 3 illustrates a typical situation in which a flowable material under test having varying characteristics is continuously passing through the test chamber 2, producing characteristic curves 18, 20 and 30, for example. Each of the curves reveals that the material under test at any given moment may have a moisture content varying between zero and ten percent. The curve 18 represents the material under test when the moisture content is approximately ten percent, producing a cutoff region 28 at a frequency 31, or approximately 2.0 GHz using the same x-axis 24 as depicted in FIG. 2. A moisture content of zero causes the cutoff region 29 to begin at frequency 39, or approximately 2.5 GHz. Assuming that the frequency of oscillator 3 is swept over a constant range of, for example, 0.4 to 4.0 GHz the cutoff frequency changes as a function of dielectric constants. This change in dielectric constant can be correlated to moisture or various other constituent variations.

Figure 4:
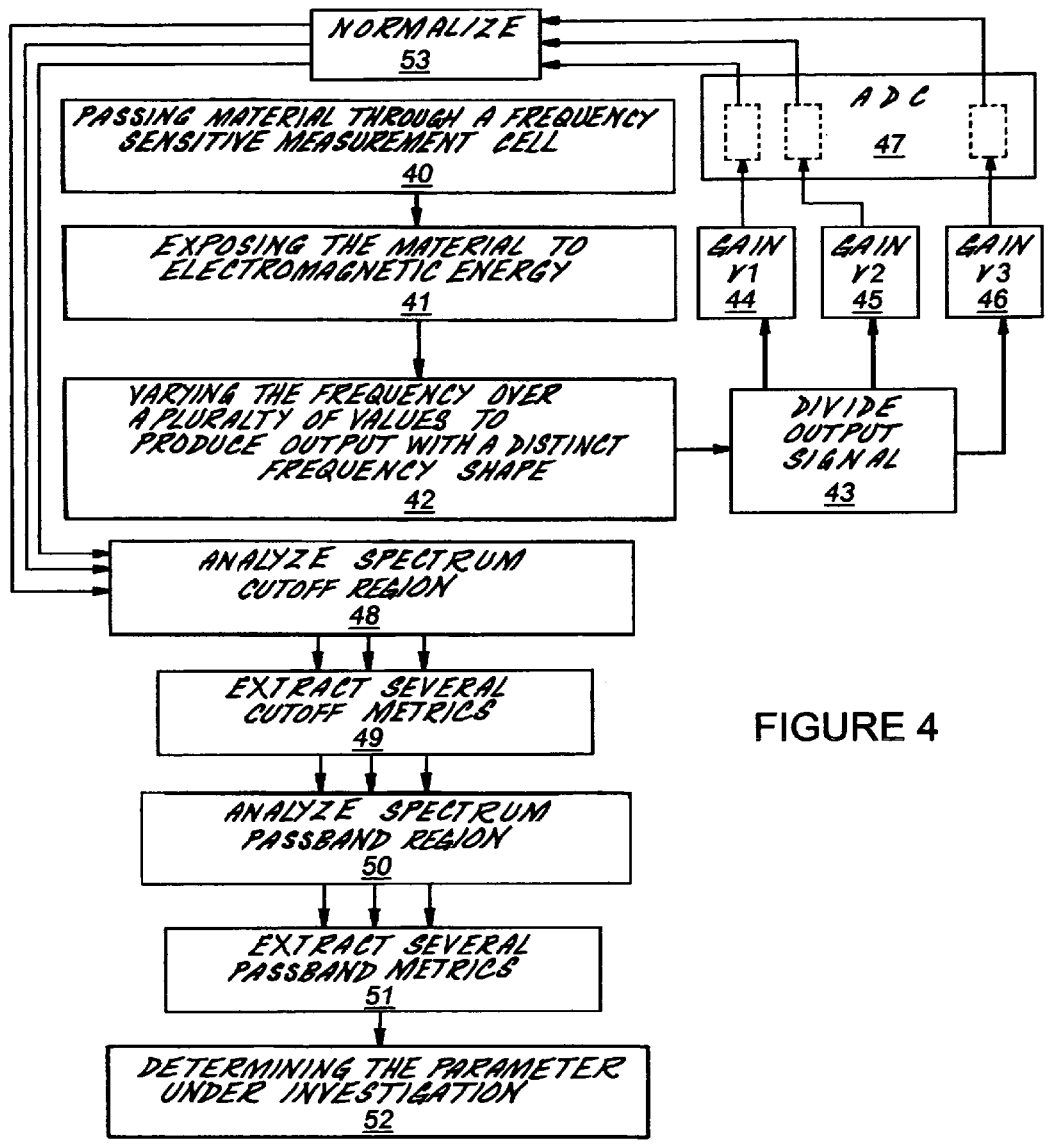
FIG. 4 is a flow chart illustrating the operation of a preferred embodiment of the present invention.
Figure 9:
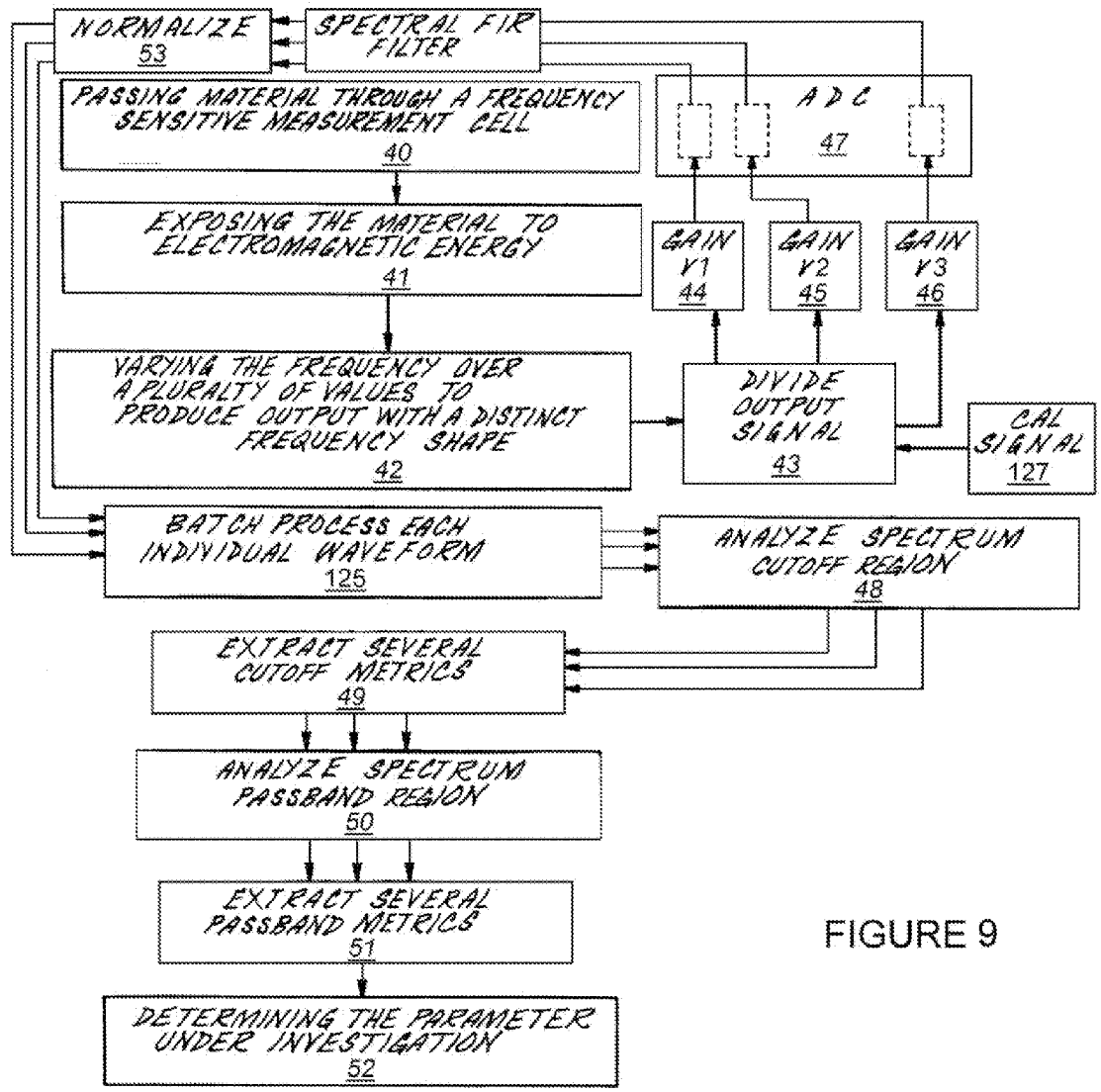
FIG. 9 is a flow chart of an alternate embodiment of the invention depicted in FIG. 4.

The steps required to implement the present invention 1 are illustrated in FIG. 4. At step 40, the material under test is introduced into the test chamber 2, typically by means of a pressurized pipe or conduit that transports the fluidized material under test. The material under test is initially subjected to electromagnetic radiation at step 41, and at step 42 the frequency of the electromagnetic radiation is varied or swept to include a segment of the radio frequency spectrum that will produce a unique response based on the characteristics of the test chamber 2 and one or more characteristics of the material being examined. The radio frequency energy exiting the test chamber 2 is frequency down converted and then divided into two or more distinct received signal paths at step 43. A first path is amplified at a first voltage gain at step 44 while a second path is amplified at a second voltage gain at step 45. One or more additional steps 46 may also be included to correspond to additional received signal paths for amplification at other voltage gain values. Referring also to FIG. 9, an alternate embodiment is illustrated depicting the addition of an additional step 125, in which the normalized data is filtered as an entire discrete waveform. In this embodiment, all of the data resulting from the electro-magnetic characterization of the material under test during a single electro-magnetic characterization event is filtered and processed in its entirety. The additional available signal data within a given background noise environment thereby improves the signal to noise ratio present in the subsequent data analysis steps 48-52.

Figure 5:
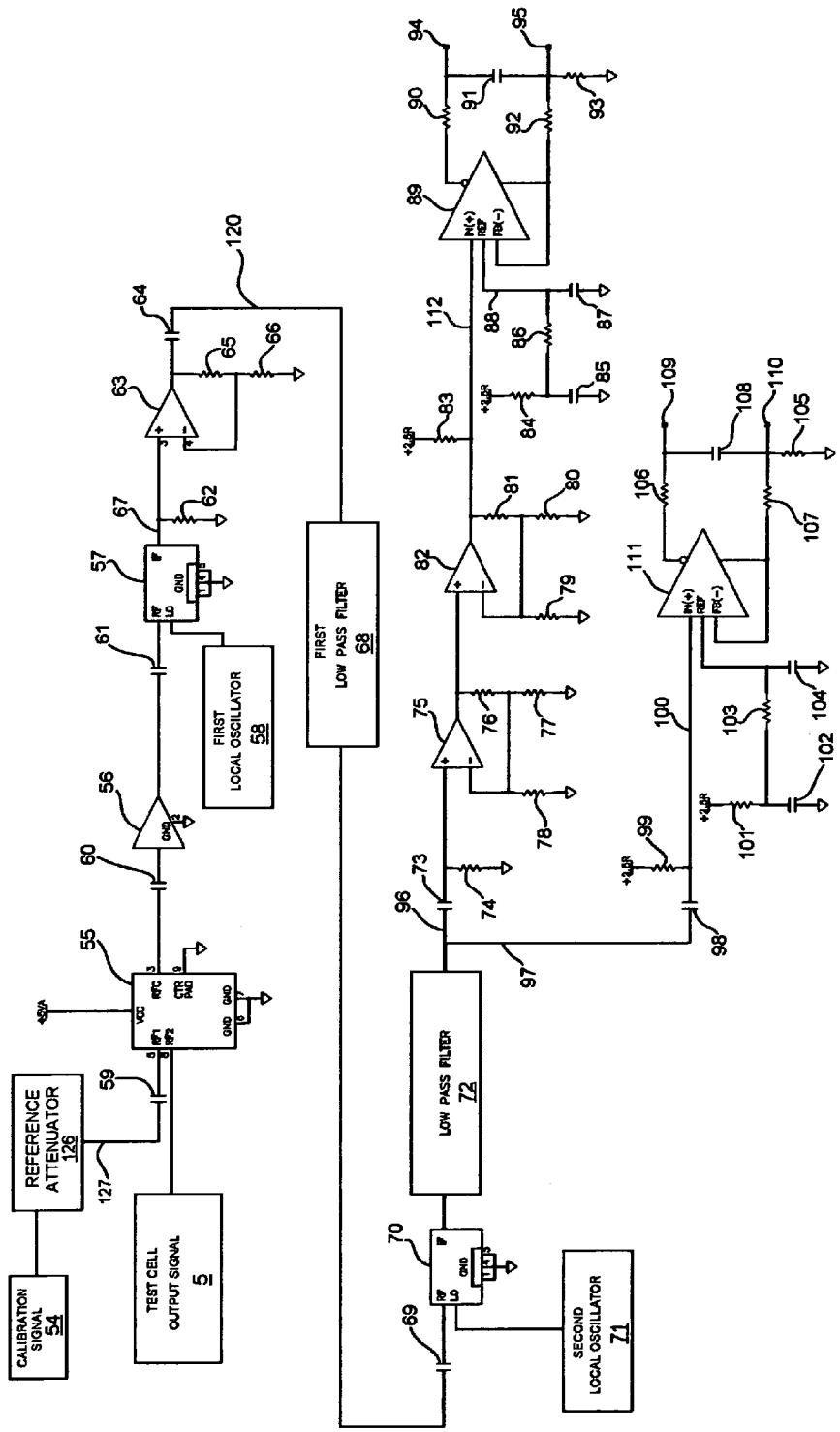
FIG. 5 is a schematic diagram of a first preferred embodiment depicted in FIG. 1.

Each of the raw analog signals produced at steps 44, 45 and 46 are subjected to individual analog to digital conversion at step 47, followed by a normalization step 53. The normalization process 53 is based on the reality that each of the individual signal paths 44, 45 and 46 will have overlapping dynamic ranges. Referring also to FIG. 5, the calibration or reference signal 54 is independent of the test cell output signal 5 and is not dependent on the properties of the material under test. The amplitude values obtained at each stepped frequency that exit the switch 55 are actually a ratio of the reading of the cell output signal 5 divided by the output of the test signal 54 after the test signal 54 has passed through reference attenuator 126. The reference attenuator 126 attenuates the amplitude of the reference signal 54 so that signal 54 is within the dynamic range of the multiple gain paths shown at ADC step 47. Typically the attenuator output signal 127 is selected less frequently than the test output signal 5. Whenever the attenuator output signal 127 is selected, the data from all gain paths gathered at ADC step 47 are stored. When the test cell signal 5 is taken, the gain data for paths 44, 45 and 46 are read and one of the paths is selected in a sequential fashion. The selected test cell value obtained from either path 44, 45 or 46 is then normalized based on the reference attenuation data that followed the path having the same gain.

Each digitized and normalized signal is separately analyzed at step 48 in order to determine the cutoff region of the spectrum for the material under test. At step 49, several cutoff parameters are extracted including, for example, frequency, slope, amplitude and intercept. Once the cutoff region has been analyzed, the passband characteristic for each received signal is evaluated at step 50, with a statistical analysis applied at step 51 to determine additional passband characteristics such as the amplitudes, slopes and curvatures corresponding to the material under test. Once the cutoff and passband characteristics have been quantified, a lookup table or other database is consulted at step 52 to determine how the value of the cutoff characteristic corresponds to a particular parameter of interest for the material under test. Typically, the signal amplitude drops with increasing frequency. Cutoff analysis provides dielectric constant information. The passband provides information on dielectric loss. Both the passband and cutoff slope provide information on conductivity losses. Hence both of these parameters are important to the overall dielectric analysis.

Referring also to FIG. 5, an actual circuit implementing the principles of the present invention includes the introduction of the test cell output signal 5 into a single pole double throw switch 55 (Hittite Microwave HMC336). The test cell output 5 is a swept or stepped frequency covering the range of 31.25 MHz to 4000 MHz. A calibration or reference signal 54 is also introduced to the switch 55 via coupling capacitor 59 (270 pf). One of the two input signals 5 or 127 is selected by the switch 55, and forwarded through coupling capacitor 60 (270 pf) to a monolithic amplifier 56 (Mini-Circuits GALI-19) whose output is sent through coupling capacitor 61 (270 pf) to become the radio frequency input to the frequency mixer 57 (Mini-Circuits ADE-42 MH). A first local oscillator (LO) signal 58 is also introduced to the mixer 57, the first local oscillator signal 58 being swept through the frequency range of approximately 42 MHz to 3989 MHz, the first LO signal 58 always being offset from the test cell output signal by a difference of approximately 10.76 MHz. The mixer 57 subtracts the test cell output signal 5 from the first LO signal 58 to create the fixed 10.76 MHz first intermediate frequency (IF) signal 67 across impedance matching resistor 62 (51 ohms).

The first IF signal 67 is an input to current feedback amplifier 63 (Analog Devices AD8001), the feedback resistance of amplifier 63 being defined by resistor 65 (620 ohms) and resistor 66 (430 ohms). The output of the amplifier 63 is coupled via capacitor 64 (330 pf) to serve as the first IF input 120 to a first low pass filter 68. The signal exiting low pass filter 68 is coupled through capacitor 69 (0.1 mfd) to the RF input of a second mixer 70, the second input to second mixer 70 being the output of second local oscillator 71. The frequency of the second local oscillator 71 is approximately 10.7 MHz, resulting in a second intermediate frequency of approximately 60 KHz that is sent through second low pass filter 72, the second low pass filter 72 having a 3 db cutoff frequency of approximately 2 MHz.

Upon exiting the second low pass filter 72, the low pass filter output signal is split into a first IF signal path 96 and a second IF signal path 97. The first IF signal path 96 is coupled through a coupling capacitor 73 (0.1 mfd) and resistor 74 (22K ohms) to a first operational amplifier 75, which has its gain set by resistors 76 (4.99K ohms), 77 (1.69K ohms) and 78 (100K ohms). The output of the first operational amplifier serves as the input to second operational amplifier 82, which has its gain determined by resistors 79 (100K ohms), 80 (1.69K ohms) and 81 (4.99K ohms). The output of the second operational amplifier 82 serves as the signal input 112 to a differential analog to digital converter driver 89 (Analog Devices ADA 4941-1). The resistor 83 (22K ohms) establishes the level of input signal 112 to driver 89, while resistors 84 (10K ohms) and 86 (12K ohms) establish the appropriate reference level for the driver 89. Bypass capacitors 85 and 87 (both 0.1 mfd) shunt undesired RF energy to ground. The differential driver 89 generates a positive output signal that is coupled through resistor 92 (27 ohms) to create noninverted output signal 95, and also generates a negative output signal that is coupled through resistor 90 (27 ohms) to create inverted output signal 94. Capacitor 91 (2200 pf) is in parallel with both output signals 93 and 94, while resistor 93 (12K ohms) is in series with capacitor 91 and ground. The output signals 93 and 94 are forwarded to analog to digital converter 47 for additional signal processing. The signal path 96 that terminates the output signals 93 and 94 represents a relatively high gain signal path.

The second IF signal path 97 is coupled through the capacitor 98 (0.22 mfd) and serves as the input to the differential analog to digital converter driver 111 (Analog Devices ADA 4941-1). The resistor 99 (22K ohms) establishes the level of input signal 100 to driver 111, while resistors 101 (10K ohms) and 103 (12K ohms) establish the appropriate reference level for the driver 111. Bypass capacitors 102 and 104 (both 0.1 mfd) shunt undesired RF energy to ground. The differential driver 111 generates a positive output signal that is coupled through resistor 107 (27 ohms) to create noninverted output signal 110, and also generates a negative output signal that is coupled through resistor 106 (27 ohms) to create inverted output signal 109. Capacitor 108 (2200 pf) is in parallel with both output signals 109 and 110, while resistor 105 (12K ohms) is in series with capacitor 108 and ground. The output signals 109 and 110 are forwarded to the analog to digital converter 47 for additional signal processing. The signal path 97 that terminates the output signals 109 and 110 represents a relatively low gain signal path.

Figure 7:
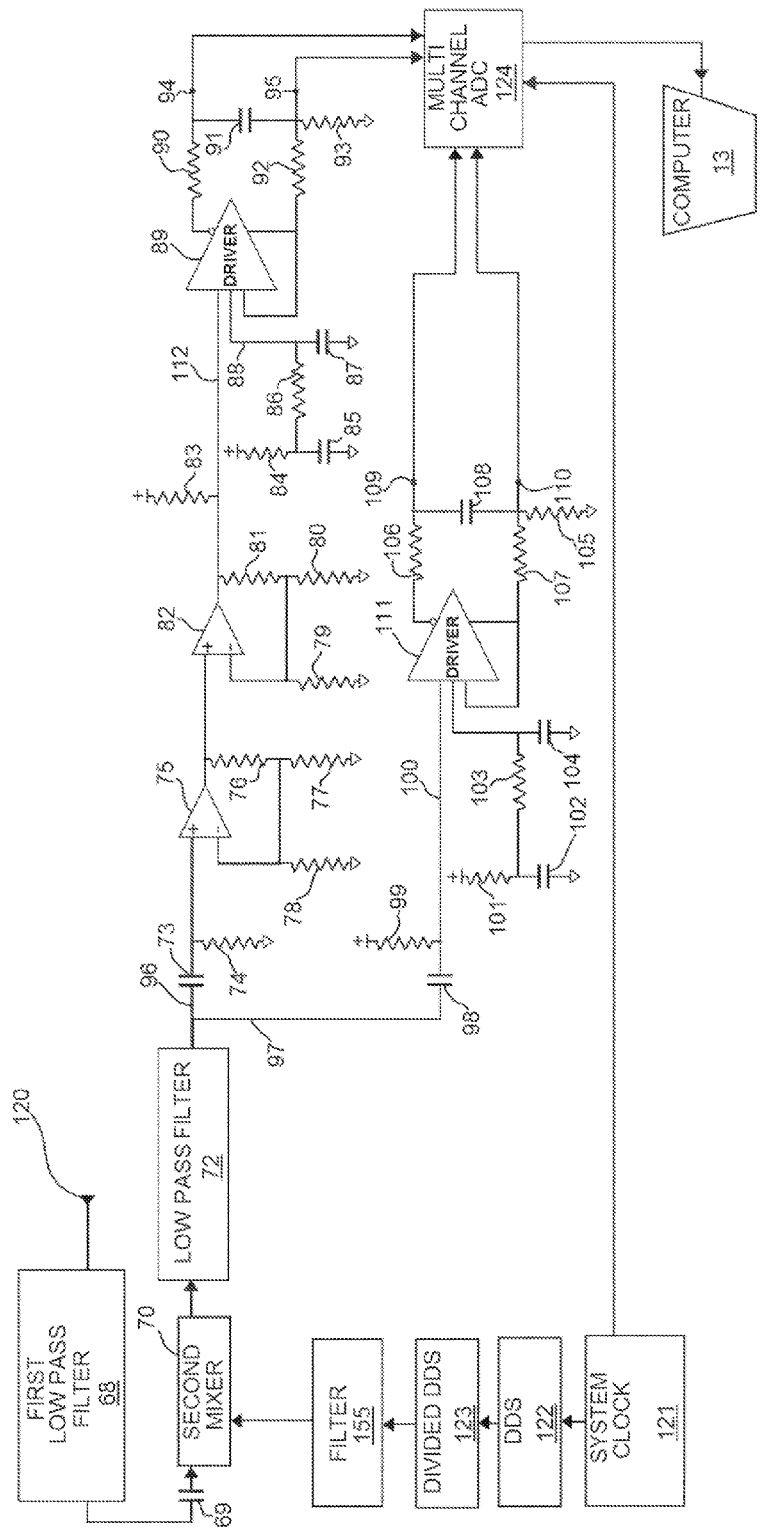
FIG. 7 is a schematic diagram of a signal amplitude measurement enhancement of the first preferred embodiment illustrated in FIG. 5.

A single system clock 121 operating at a frequency of 86.08 MHz is the original source of all timing signals utilized in the system 1. As seen in FIG. 7, the system clock 121 serves as the timing signal for the Direct Digital Synthesizer (DDS) 122. The DDS 122 is capable of operating at a selected fixed frequency with extreme resolution within a wide spectrum of frequencies, and is typically operated at a frequency that will yield an integral relationship with all other directly or indirectly sampled frequencies within the system 1. The frequency of the second local oscillator as produced by the DDS divider 123 is approximately 10.7 MHz, with any spurious components of the divided DDS signal 123 being removed by the filter 155.

Since the first intermediate frequency is 10.76 MHz, the mixing product difference produced by mixer 70 results in a second intermediate frequency of approximately 60 KHz, the latter being the frequency that is actually sampled to determine the signal characteristics of interest. In order to maintain the desired integral relationships between the frequency of the system clock 121, the divided DDS local oscillator and the approximately 60 KHz sampled frequency, the output of the DDS 122 is reduced by the DDS divider 123 to produce a lower integrally related frequency reference to serve as the local oscillator. The signal produced by the DDS divider 123 may be used directly as the local oscillator, or the divided signal may be used as a reference trigger signal by a separate oscillator to independently create a 10.7 MHz signal. Further, the system clock 121 also serves as the time base and triggering mechanism for the multi channel ADC 124 which sets the length of time during which sampling of the approximately 60 KHz second intermediate frequency occurs.

In the present system 1, the frequency of the signal being sampled is the second intermediate frequency of 60 KHz, which remains fixed regardless of the actual frequency of the multi frequency source 3. The rate at which this frequency is sampled by the computer 13 is also fixed. The time or duration of the sampling period is:

$$T=C/R, \text{ where}$$

T=the duration of the sampling period;
C=the sample count; and
R=the sample rate, which is a constant.

During the sampling period, the number of cycles of the sampled waveform is:

$$N=T/F, \text{ where}$$

N=the number of cycles sampled;
T=the duration of the sampling period; and
F=the frequency of the signal being sampled.

Figure 6:
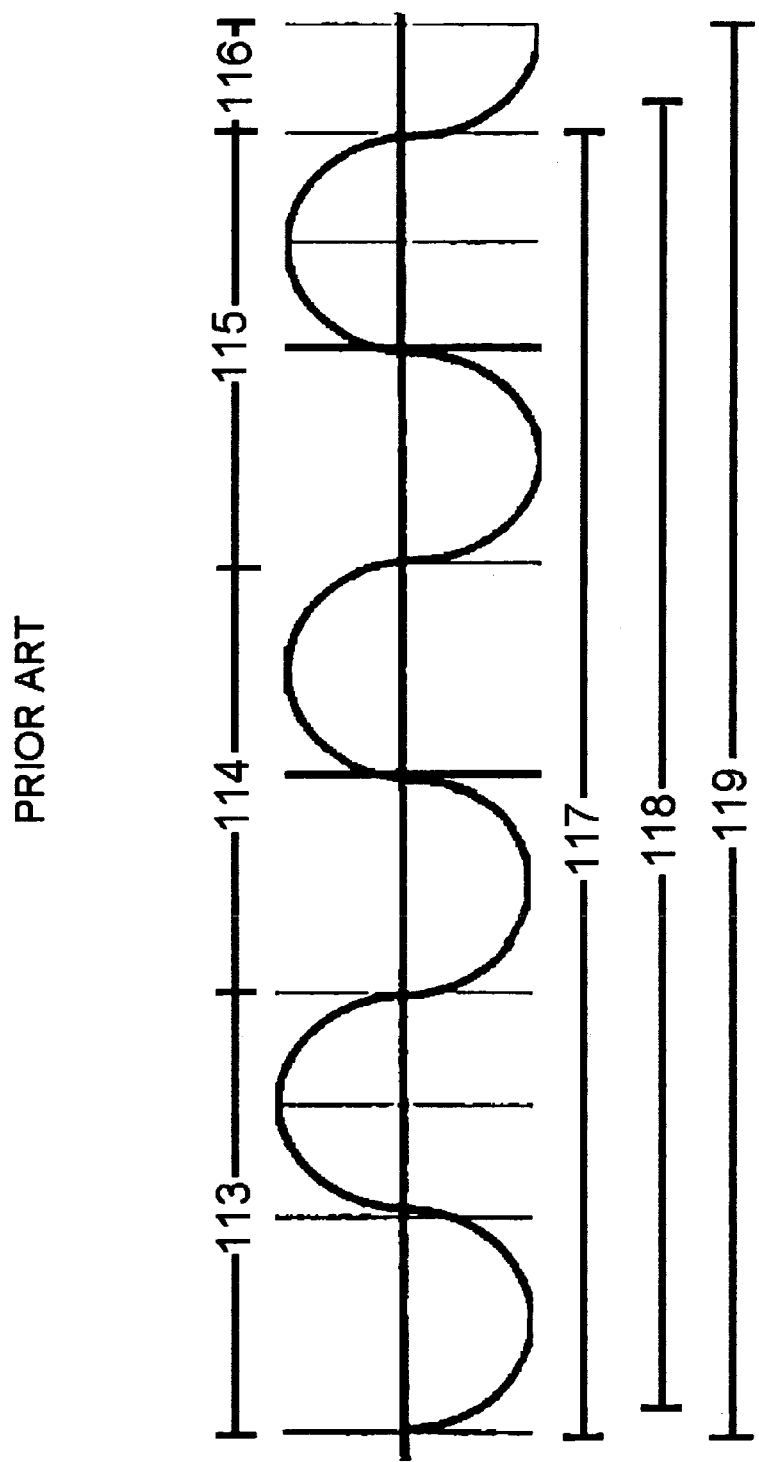
FIG. 6 is a prior art depiction of waveform sampling parameters.

In the present invention, the sample count C and the number of cycles N are both caused to be whole numbers or integers. In other words, the time of the sampling period must have a duration that does not truncate any portion of a complete cycle of the sampled frequency F as discussed earlier with reference to FIG. 6. A number of frequency relationships in a given system 1 may satisfy this requirement. In the present system 1, for example, the sample rate is fixed at 206.923 KHz, meaning that each sample represents a 4.83272 uSec portion of the signal. The objective is to cause samples taken to correspond to an integer number of cycles of the approximate 60 kHz waveform. For example, if waveform is sampled 170 times, this corresponds to a sampling interval of 0.82156 mSec. At a frequency of 60 kHz this interval would include 42.2937 cycles, not an integer. Thus the DDS is set to generate a second LO frequency that will result in an IF frequency of 59.64253394 kHz instead of 60 kHz. In the sample interval, this choice of intermediate frequency yields exactly 49 cycles of the IF waveform. This ensures that no portion of a complete sampled waveform cycle will be truncated.

Figure 8:
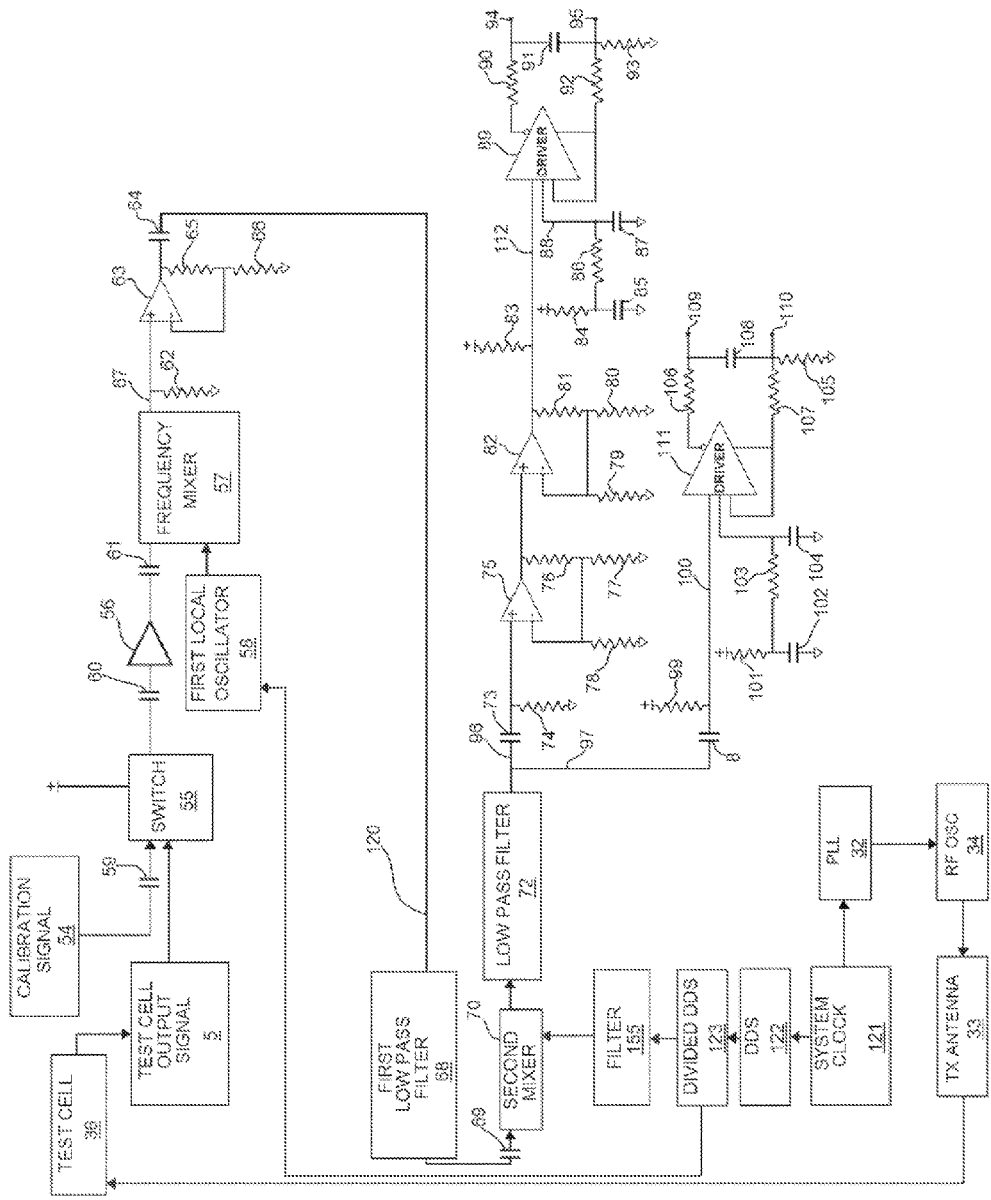
FIG. 8 is a schematic diagram depicting a synchronous signal generation enhancement of the first preferred embodiment illustrated in FIG. 5.

Referring also to FIG. 8, the synchronization of all transmitted and received signals can be better appreciated. Both the first local oscillator 58 and the second local oscillator as created by divided DDS 123 are implemented as phase locked loop circuits, typically utilizing the Analog Devices ADF4153 fractional-N frequency synthesizer integrated circuit. The system clock 121 also serves as the baseline synchronizing signal for phase locked loop 32 which controls the radio frequency (RF) oscillator 34. The transmitting antenna 33 is excited by the RF oscillator 34 and electro-magnetically characterizes a material under test within the test cell 36. The received RF energy, after passing through the test cell 36, generates the test cell output signal 5 which is then processed as previously described. In this manner, the single system clock 121, acting through the phase locked loop controlled oscillators 34 and 58 as well as the DDS divider 123, causes all reference signals in the RF, IF and AF portions of the system 1 to be phase synchronous, thereby simplifying and improving the quality of analysis of the test cell output signal 5.

Figure 10:
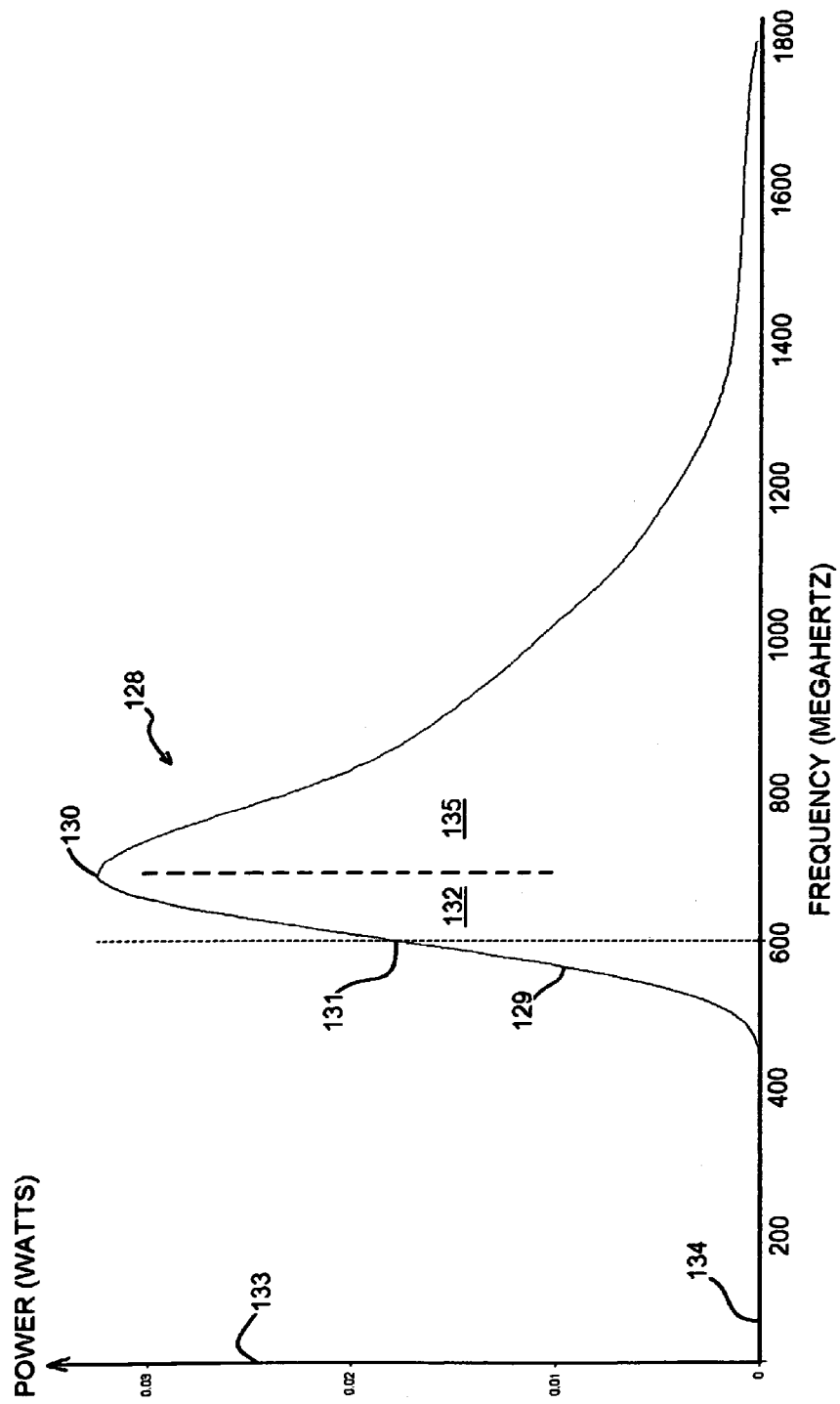
FIG. 10 is a graph of amplitude versus frequency for an exemplary material undergoing electro-magnetic characterization in the test chamber depicted in FIG. 1.

Referring also to FIG. 10, the nature of the analysis performed by the system 1 can be better appreciated. A response curve 128 results from electro-magnetic characterization of a material under test as is resides within the test chamber 2. The curve 128 includes a region 129 of generally positive slope, the amplitude of which may be read on y-axis 133 at any particular frequency as depicted on x-axis 134. Point 131 corresponds to the inflection point which in this example is approximately 600 MHz. Region 130 of the curve 128 corresponds to the peak amplitude of curve 128. The entire region 132 to the left of the peak 130 corresponds to the cutoff area while the region 135 to the right of peak 130 corresponds to the pass band characteristics of the curve 128. Together the pass band characteristics and the cutoff frequency permit the dielectric constant of the material under test to be determined. The desirability of having a precise and undistorted curve 128 in order to accurately determine the inflection point 131 and the peak value 130 is apparent.

Figure 11:
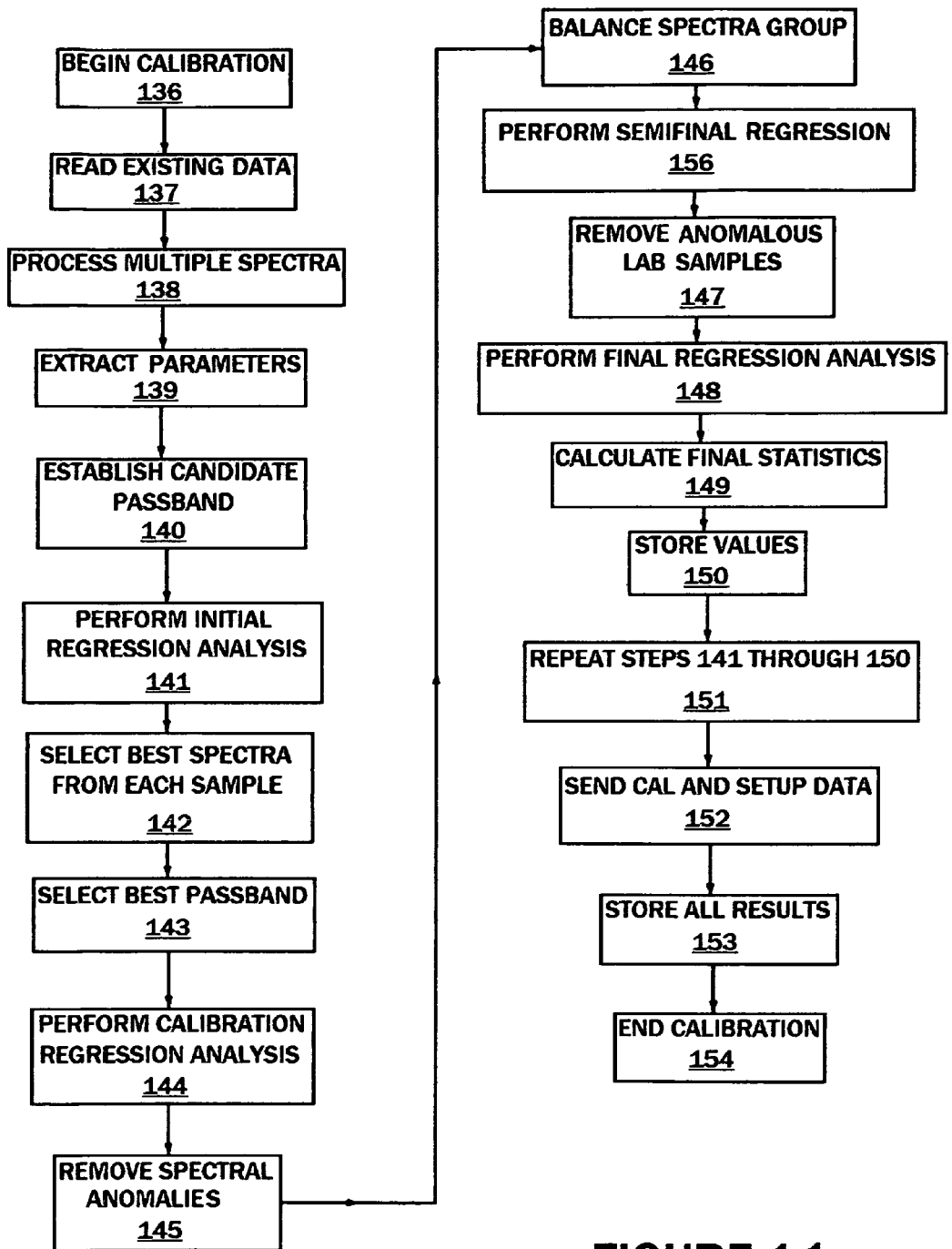
FIG. 11 is a flow chart of the calibration program employed as a part of the system depicted in FIG. 1.

The calibration program utilized in the present invention is for determination of the idealized curve 128 and its associated parameters is depicted in FIG. 11. At step 136 the computer 13 begins the calibration routine, which may be initiated as necessary at the beginning of and throughout the operation of a guided microwave analysis session. This is followed by the reading and processing of existing data at step 137. Typically, reference data from prior production sessions exists in a reference file stored within or accessible by the computer 13. A typical reference file contains values that have already been identified as acceptable for the proposed MUT, and a list of items may be generated for use by a setup file that initiates and defines the frequency sweep. Data to be extracted from prior reference files includes calibration spectra, the number of analytes to be considered, prior laboratory reference values and their association with a set of idealized spectra, the calibration temperatures, the calibration frequency ranges, as well as sample and spectral tagging data, derived either from the initial reference values or from the previous calibration iteration.

The next step 138 processes multiple spectra associated with a plurality of typical test items that are laboratory samples representative of the MUT to be processed during a guide wave spectroscopy session. An FIR filtering protocol is applied to each individual linear spectrum in order to obtain an undistorted curve such as the curve 128 depicted in FIG. 10. The logarithmic representation of each spectrum is calculated at step 138. The extraction of the cutoff frequency and associated parameters associated with each spectrum is performed at step 139. The calculated parameters include the cutoff frequency based on the centroid of the peak slope region, the absolute and relative cutoff slopes, the cutoff amplitude and the frequency axis intercept of the frequency cutoff line.

A candidate pass band region is derived at step 140 by determining the frequency corresponding to the peak amplitude of each spectrum. The single highest frequency found among all spectra establishes the beginning of the overall candidate pass band region while the end of the candidate pass band region is at the end of that spectrum. An initial regression analysis is then performed at step 141 for each analyte being processed in order to determine how well each set of samples for a particular type of MUT agrees with every other spectrum in the sample set. The desired quantitative data is extracted from the candidate pass band region and any previously stored calibration data is examined to verify that none of the prior data is within the top or bottom fifteen percent of the candidate pass band. Based on the results of the initial regression analysis the most representative spectrum is identified at step 142 using the spectra produced from the laboratory samples tested. This is accomplished by calculating the mean residual for all spectra in the sample set and then eliminating the individual spectrum having the residual value that is furthest from the mean residual. The mean residual for the remaining spectra is then calculated and again the individual spectrum having a residual value furthest from the mean value is discarded. This process is repeated until only one spectrum remains, which is then considered to be the best representative spectrum for subsequently determining the best pass band boundary definition.

Using the logarithmic representation of spectra created at step 138 and the candidate pass band region derived at step 140 the best or most typical pass band region is determined at step 143. A table of standard deviations is then created corresponding to the pass band width and start frequency by performing a regression analysis and storing the standard deviations. After a set of standard deviation tables has been created, the position in the table having the lowest standard deviation is identified, thereby establishing a frequency around which another regression analysis can be performed. Upon completion of a table of standard deviations based on the smaller frequency steps, the lowest standard deviation value present in the table defines the start frequency and passband width to be used while electro-magnetically characterizing the particular analyte being processed. A calibration regression analysis is performed at step 144 with all spectra created at step 138 and using the newly established best pass band frequency range.

Any anomalous spectral data is removed at step 145. For each set of spectra associated with a test sample, the mean standard residual is determined. A spectrum is a candidate for removal if the standard residual is furthest from the mean standard residual for the entire spectra set. The candidate spectrum should be removed as not being the representative of the sample if the following two conditions are met. First, the difference from the mean standard residual exceeds a predetermined percentage of a "leave out one" standard residual threshold for individual sample spectra. For example, if the "leave out one" standard residual for sample spectra is 2, and the percentage threshold for spectra is 25%, the standard residual threshold of an individual spectrum from the mean will be 0.5. The "leave out one" calculation for a given sample refers to the technique of calculating a value that is determined by ignoring that particular sample. The "leave out one" residual for a particular sample is that sample's residual when that sample is not included in the regression analysis. A set of "leave out one" values for each sample is determined by recalculating the regression for each sample with that sample eliminated from the regression analysis. Assuming that the first criterion for candidate spectrum removal is met, the second required criterion for removing the candidate spectrum is that removal will not cause the set of remaining spectra to fall below a predetermined threshold value. For example, if the sample set is 12 and the minimum threshold value is 3, then no more than 9 spectra may be removed, regardless of the departure of an individual spectrum from the standard residual. The foregoing process is repeated until each remaining candidate spectrum fails to meet the removal criteria.

The group of spectra associated with a laboratory or reference sample of a potential MUT must be the same size as every other such group of spectra. The number of spectra representing a laboratory sample in the calibration regression analysis is a weighting factor that affects the influence of that particular sample on the calibration result. Unbalanced group sizes would give some lab samples more weight than others. The balancing of spectra group size is accomplished at step 146. For any spectra group, if the number of spectra in that group is larger than the number of spectra in the smallest group, then that spectra group must be reduced in size. The group size reduction process is accomplished by determining the mean standard residual (SR) for spectra that have not already been removed for other reasons. The individual spectrum having the SR that is furthest from the mean SR is then removed. This process is repeated until that group size is equal to the smallest spectra group size. The semifinal regression analysis is then recalculated using the remaining spectra at step 156.

The next step 147 removes anomalous laboratory samples from the calibration process calculations. The general removal sequence is to establish a candidate worst sample and then determine if this candidate meets all of the criteria for being removed. If so, that sample is removed and the remaining samples are reprocessed using the foregoing regression analysis methods. If a sample does meet all of the removal criteria, then the process is repeated for the next candidate sample until no candidate worst sample meets all of the removal criteria. All of the repeated calibration regressions contained in the following procedures use of the spectra that have not been removed in step 145. In each case, the predicted value of a sample is the mean predicted value for the spectra in the spectra group.

To initiate the removal procedure of step 147, base statistic values should be computed for all samples, including standard deviation (SD), R squared value (RSV), predicted value of each sample, the residual for each sample, that is, the difference between laboratory sample value and the predicted value, and the standard residual (SR) for each sample. Next, for each sample the following "leave out one" value calculations previously discussed should be performed, including standard deviation (SD), R squared value (RSV), predicted value, residual, standard residual (SR), percent improvement in SD relative to base SD, percent improvement in RSV relative to base RSV and sample population density factor (SPDF). The SPDF is the ratio of the average space or distance between each lab value sample and its nearest neighbor. A low value means that the area is less well represented, making the sample more valuable. Then determine a use weighting factor (UWF) based on the SPDF and a predetermined importance factor, where the default importance factor is zero. In the case where the importance factor is zero the UWF will be 1.0 and thus have no effect on the influence of the sample in subsequent calibration calculations.

The candidate sample to be removed is the one with highest "leave one out" calculation. The candidate sample is removed if all of the four following conditions are met. First, the remaining sample count is greater than the predetermined minimum sample count, where the default value is 90% of the laboratory samples. A 90% remaining sample count corresponds to an approximate 1.7 sigma value for a Gaussian distribution. Second, the "leave one out" standard residual (SR) exceeds a predetermined threshold. Typical values range from 1.5 to 2.0. If the value is set to zero then the sample count threshold dominates the anomalous spectra determination. Third, the standard deviation improvement relative to the base value is greater than predetermined threshold, where the default value is zero, meaning that the standard deviation improvement has no effect on subsequent calculations. The use weighting factor (UWF) previously discussed is applied so that samples with no nearby neighbors are less likely to be removed. Finally, the R squared value (RSV) improvement relative to the base value is greater than a predetermined threshold where the default is zero and thus the RSV improvement has no effect on subsequent calculations. The UWF is applied so that samples with no nearby neighbors are less likely to be removed. Setting individual threshold parameters to zero will have the effect of removing those parameters from subsequent calculations, leaving the remaining parameters to control the spectra removal process. By removing all but one parameter, the effects of that threshold parameter on the process become apparent. The foregoing calculations are repeated until no more candidate samples satisfy the removal criteria. Upon completion of the foregoing, the final regression analysis is performed at step 148. The final regression analysis generates calibration coefficients and subsequently calculates the base statistics at step 149.

The final statistics calculated at step 148 are the base standard deviation (SD) and the base R squared value (RSV). The statistics for each laboratory sample are also calculated, including predicted value, residual, standard residual (SR), and the following "leave out one" values: predicted value, standard deviation, standard deviation improvement relative to the base standard deviation value, standard residual, R squared value and the R squared value improvement relative to the base R squared value. All of these statistics are stored at step 150 for a particular analyte. The steps 141 through 150 are repeated at step 151 until the calibration data for each analyte has been obtained. At step 152 all of the initial calibration and setup data for each analyte is combined with the calibration results which are stored at step 153 and the calibration process is thus completed at step 154. Step 137 also includes saving the parameter values needed for subsequent data processing iterations.

One can appreciate that the present invention will find many applications in signal processing where a large dynamic range is needed without the deleterious effects of an automatic gain control circuit, as well as those situations where only complete waveforms should be sampled during the measurement and analysis phase in order to insure greater accuracy of the results. While specific implementation of the invention has been described, many variations of specific circuitry are included within the scope of the appended claims. For example, the normalization scheme described herein may be adapted to gain paths of varying numbers. When more than two gain paths are used one may employ multiple attenuators in the reference signal path in order to provide overlapping ranges between the various gain paths. In operation, all of the reference signals can be cross calibrated with each other. In the case of five gain paths, one would use four reference attenuators. Each attenuator would be set to provide a signal to two of the gain paths. Adjacent gain path amplitude measurements would be periodically obtained and cross calibrated. Each cell reading would then use the calibrated reference normalizing value corresponding to the gain path used for that particular cell reading. An additional variation on the present invention would include continually seeking cell readings that fall within overlapping gain path dynamic ranges. Whenever such an overlapping pair of signals is found, the system 1 would use that data to determine a gain ratio between the two gain paths that produced each of the overlapping signals. The ratio can then be continuously averaged, by using FIR or IIR techniques, with previous ratio data in order to obtain a current gain ratio value for use in subsequent calculations.

I claim:

1. A system for processing a signal received while operating a guided microwave spectroscopy device, comprising:
    (a) a variable frequency signal source;
    (b) a test chamber, the test chamber containing a material under test;
    (c) a received signal path, the received signal path containing radio frequency energy initially generated by the variable frequency signal source after the radio frequency energy has been altered by passing through the material under test;
    (d) a plurality of received signal amplifiers, each received signal amplifier being interconnected to the received signal path, each received signal amplifiers producing an output signal, and;
    (e) a computer, the computer being interconnected to the plurality of received signal paths, the computer being programmed to determine parameters of the material under test in response to the output signal produced by each of the plurality of received signal amplifiers.

2. The system of claim 1, wherein each received signal amplifier further comprises a fixed voltage gain, the fixed voltage gain of each received signal amplifier differing from the fixed voltage gain of every other amplifier.

3. The system of claim 2, wherein each received signal amplifier is interconnected in a parallel relationship with every other received signal amplifier.

4. The system of claim 3, wherein each received signal amplifier is interconnected in a series relationship with the received signal path.

5. The system of claim 4, wherein the fixed voltage gain of each received signal amplifier is related to the fixed voltage gain of every other signal amplifier by an integral exponential power of two.

6. The system of claim 5, wherein the computer normalizes each output signal from each received signal amplifier so as to create data that is suitable for comparative analysis of each output signal.

7. The system of claim 6, further comprising a sample rate timer, the sample rate timer being interconnected to the computer and to the output signal of each received signal amplifier, the sample rate timer determining a period of time during which sampling of each output signal occurs.

8. The system of claim 7, further comprising:
(a) a first local Oscillator operating at a first frequency;
(b) a first mixer, the first mixer receiving a signal from the first local oscillator and the variable frequency signal source, the first mixer producing a first intermediate frequency output signal;
(c) a second local oscillator operating at a second frequency;
(d) a second mixer, the second mixer receiving the first intermediate frequency output signal and a signal from the second local oscillator, thereby producing a second intermediate frequency, wherein the second intermediate frequency is sampled to determine parameters of the material under test.

9. The system of claim 8, further comprising:
(a) a digital frequency synthesizer; and
(b) a system clock, the system clock being interconnected to the digital frequency synthesizer and the sample rate timer, the system clock causing a signal produced by the digital frequency synthesizer and a sampling period of the sample rate timer to be synchronized.

10. The system of claim 9, wherein the second local oscillator is interconnected to the digital frequency synthesizer, the second frequency produced by the second local oscillator being derived from the digital frequency synthesizer, thereby causing synchronicity between formation of waveforms constituting the second intermediate frequency and the sampling period generated by the sample rate timer.

11. The system of claim 10, wherein the period of time during which sampling of each output signal occurs has a duration that causes only a substantially exact whole number of complete output signal waveform cycles to be sampled.

12. The system of claim 11, wherein the period of time during which sampling of each output signal occurs is:

$T=C/R$, where

T=duration of the period of time during which sampling of each output signal occurs;
C=sample count; and
R=sample rate, which is a constant.

13. A guided microwave spectroscopy signal processing device, comprising:
(a) a variable frequency oscillator adapted to radiate electromagnetic energy through an object;
(b) a receiver, the receiver being adapted to intercept at least a portion of the electromagnetic energy after the electromagnetic energy has passed through the object, the receiver further comprising:
(i) a first signal processing path having a first amplification factor;
(ii) a second signal processing path having a second amplification factor;
(c) a computer, the computer independently sampling and independently processing the first signal processing path and the second signal processing path in order to determine at least one property of the object; and
(d) a system clock, the system clock synchronizing the computer such that substantially all signal samples recorded by the computer during a sampling period contain a substantially whole number of complete signal waveform cycles.

14. The signal processing device of claim 13, further comprising:
(a) a first local oscillator, the first local oscillator generating a first fixed frequency that is mixed with a portion of the electromagnetic energy intercepted by the receiver so as to create a first intermediate frequency; and
(b) a second local oscillator, the second local oscillator generating a second fixed frequency that is mixed with the first intermediate frequency so as to create a second intermediate frequency, wherein the first fixed frequency and the second fixed frequency are derived from the system clock so as to synchronize generation of the first and second fixed frequencies with the sampling period generated by the computer.

15. The signal processing device of claim 14, further comprising:
(a) a first phase locked loop circuit, the first phase locked loop circuit controlling the first local oscillator, the first phase locked loop circuit receiving a system reference timing signal from the system clock; and
(b) a second phase locked loop circuit, the second phase locked loop circuit controlling the second local oscillator, the second phase locked loop circuit receiving the system reference timing signal from the system clock, thereby causing signals generated by the first local oscillator and the second local oscillator to be phase synchronous.

16. The signal processing device of claim 15, wherein the first signal processing path and the second signal processing path are derived from a single heterodyned output created by mixing the second fixed frequency with the first fixed frequency, the first and second signal processing paths both operating at substantially the second intermediate frequency.

17. The signal processing device of claim 16, wherein the computer normalizes a first amplitude of the first signal processing path and a second amplitude of the second signal processing path in response to a relationship between the first amplification factor and the second amplification factor.

18. The signal processing device of claim 17, wherein each signal sample derived from each whole number of waveform cycles is filtered and subsequently processed as a single discrete batch.

19. A method of processing an electromagnetic signal produced in response to electro-magnetic characterization of an object by a variable frequency oscillator, comprising the steps of:
(a) receiving the signal;
(b) dividing the signal into a plurality of signal paths;
(c) amplifying each of the plurality of signal paths at a different amplification factor;
(d) normalizing each amplified signal to produce a normalized signal; and (e) processing each normalized signal to determine at least one characteristic of the object.

20. The method of processing an electromagnetic signal of claim 19, further comprising the step of calibrating the variable frequency oscillator to optimize determination of at least one characteristic of the object, calibrating the variable frequency oscillator comprising the steps of:
(a) sequentially electro-magnetically characterizing a plurality of laboratory samples of the object;
(b) creating a plurality of spectra in response to electro-magnetically characterizing each sample object;
(c) determining a cutoff frequency and passband for each spectrum;
(d) performing a plurality of regression analyses on data derived from each spectrum composing the plurality of spectra;
(e) identifying a most representative spectrum based on the plurality of regression analyses; and
(f) initializing and controlling the variable frequency oscillator to operate in manner most likely to reproduce the most representative spectrum whenever a subsequent object having acceptable characteristics is electro-magnetically characterized by the variable frequency oscillator.

* * * * *